United States Patent
Mishra et al.

(10) Patent No.: US 7,920,924 B2
(45) Date of Patent: *Apr. 5, 2011

(54) ESTIMATING FLAP THICKNESS FOR COCHLEAR IMPLANTS

(75) Inventors: Lakshmi Narayan Mishra, Valencia, CA (US); Michael A. Faltys, Northridge, CA (US)

(73) Assignee: Advanced Bionics, LLC, Valencia, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 12/244,082

(22) Filed: Oct. 2, 2008

(65) Prior Publication Data

US 2009/0030485 A1  Jan. 29, 2009

Related U.S. Application Data

(63) Continuation of application No. 11/016,604, filed on Dec. 16, 2004, now Pat. No. 7,450,994.

(51) Int. Cl.
*A61N 1/00* (2006.01)
(52) U.S. Cl. ...................................................... 607/57
(58) Field of Classification Search .............. 607/55–57, 607/60, 61
See application file for complete search history.

(56) References Cited

U.S. PATENT DOCUMENTS

| | | |
|---|---|---|
| 3,522,811 A | 8/1970 | Schwartz |
| 3,751,605 A | 8/1973 | Michelson |
| RE30,366 E | 8/1980 | Rasor et al. |
| 4,400,590 A | 8/1983 | Michelson |
| 4,414,979 A | 11/1983 | Hirshorn et al. |
| 4,495,384 A | 1/1985 | Scott et al. |
| 4,573,481 A | 3/1986 | Bullara |
| 4,612,934 A | 9/1986 | Borkan |
| 4,793,353 A | 12/1988 | Borkan ........................ 607/60 |
| 4,819,647 A | 4/1989 | Byers et al. |
| 4,905,285 A | 2/1990 | Allen et al. |
| 5,002,053 A | 3/1991 | Garcia-Rill et al. |
| 5,042,084 A | 8/1991 | Daly |
| 5,105,811 A | 4/1992 | Kuzma |
| 5,193,540 A | 3/1993 | Schulman et al. |
| 5,211,175 A | 5/1993 | Gleason et al. |
| 5,257,634 A | 11/1993 | Kroll |
| 5,358,514 A | 10/1994 | Schulman et al. |

(Continued)

FOREIGN PATENT DOCUMENTS

WO 00/01200 1/2000

(Continued)

OTHER PUBLICATIONS

U.S. Appl. No. 10/188,465, filed Jul. 2, 2002, Kuzma.
U.S. Appl. No. 10/364,433, filed Feb. 11, 2003.
U.S. Appl. No. 11/008,869, filed Dec. 9, 2004, P.A. Segel.
U.S. Appl. No. 11/089,171, filed Mar. 24, 2005, T. W. Hahn.
U.S. Appl. No. 11/122,648, filed May 5, 2005, G. A. Griffith.

(Continued)

*Primary Examiner* — George Manuel
(74) *Attorney, Agent, or Firm* — Wong, Cabello, Lutsch, Rutherford & Brucculeri LLP

(57) ABSTRACT

A flap thickness measurement system includes a reference cochlear stimulation system. The reference cochlear stimulation system includes a sound processor, a transmitter that transmits a telemetric signal, and a cochlear stimulator having a receiver that receives the telemetric signal and transmits a signal back to the transmitter. The system further includes one or more flap simulators having one or more known thicknesses that is positioned between the transmitter and receiver. Also included is a microprocessor that receives and processes data representative of tank voltage from the reference cochlear stimulation system.

23 Claims, 6 Drawing Sheets

U.S. PATENT DOCUMENTS

| | | | |
|---|---|---|---|
| 5,366,493 | A | 11/1994 | Scheiner et al. |
| 5,405,367 | A | 4/1995 | Schulman et al. |
| 5,479,522 | A | 12/1995 | Lindemann et al. |
| 5,591,217 | A | 1/1997 | Barreras |
| 5,601,617 | A | 2/1997 | Loeb et al. |
| 5,603,726 | A | 2/1997 | Schulman et al. |
| 5,626,629 | A | 5/1997 | Faltys et al. |
| 5,721,783 | A | 2/1998 | Anderson |
| 5,741,316 | A | 4/1998 | Chen et al. |
| 5,776,172 | A | 7/1998 | Schulman et al. |
| 5,824,022 | A | 10/1998 | Zilberman et al. |
| 5,876,425 | A | 3/1999 | Gord et al. |
| 5,938,691 | A | 8/1999 | Schulman et al. |
| 5,991,419 | A | 11/1999 | Brander |
| 5,991,664 | A | 11/1999 | Seligman |
| 6,002,966 | A | 12/1999 | Loeb et al. |
| 6,052,624 | A | 4/2000 | Mann |
| 6,064,913 | A | 5/2000 | Irlicht et al. |
| 6,067,474 | A | 5/2000 | Schulman et al. |
| 6,078,838 | A | 6/2000 | Rubinstein |
| 6,092,531 | A | 7/2000 | Chen et al. |
| 6,129,753 | A | 10/2000 | Kuzma |
| 6,154,677 | A | 11/2000 | Leysieffer |
| 6,154,678 | A | 11/2000 | Lauro .................. 607/115 |
| 6,157,861 | A | 12/2000 | Faltys et al. |
| 6,181,969 | B1 | 1/2001 | Gord |
| 6,185,452 | B1 | 2/2001 | Schulman et al. |
| 6,195,585 | B1 | 2/2001 | Karunasiri et al. |
| 6,198,971 | B1 | 3/2001 | Leysieffer |
| 6,205,360 | B1 | 3/2001 | Carter et al. |
| 6,208,882 | B1 | 3/2001 | Lenarz et al. |
| 6,212,431 | B1* | 4/2001 | Hahn et al. ............. 607/61 |
| 6,216,045 | B1 | 4/2001 | Black .................. 607/122 |
| 6,219,580 | B1 | 4/2001 | Faltys et al. |
| 6,246,911 | B1 | 6/2001 | Seligman |
| 6,249,704 | B1 | 6/2001 | Maltan et al. |
| 6,272,382 | B1 | 8/2001 | Faltys et al. |
| 6,289,247 | B1 | 9/2001 | Faltys et al. |
| 6,295,467 | B1 | 9/2001 | Kollmeier et al. |
| 6,308,101 | B1 | 10/2001 | Faltys et al. |
| 6,393,325 | B1 | 5/2002 | Mann et al. |
| 6,415,185 | B1 | 7/2002 | Maltan |
| 6,449,372 | B1 | 9/2002 | Greminger |
| 6,516,227 | B1 | 2/2003 | Meadows et al. |
| 6,549,633 | B1 | 4/2003 | Westermann |
| 6,700,982 | B1 | 3/2004 | Geurts et al. |
| 6,728,578 | B1 | 4/2004 | Voelkel .................. 607/56 |
| 6,810,289 | B1 | 10/2004 | Shaquer |
| 6,826,430 | B2 | 11/2004 | Faltys et al. |
| 6,842,647 | B1 | 1/2005 | Griffith et al. |
| 6,915,166 | B1 | 7/2005 | Stecker et al. |
| 7,200,504 | B1 | 4/2007 | Fister .................. 702/75 |
| 7,203,548 | B2 | 4/2007 | Whitehurst et al. ........ 607/39 |
| 7,242,985 | B1 | 7/2007 | Fridman et al. ......... 607/56 |
| 7,277,760 | B1 | 10/2007 | Litvak et al. .......... 607/56 |
| 7,292,890 | B2 | 11/2007 | Whitehurst et al. ........ 607/45 |
| 7,308,303 | B2 | 12/2007 | Whitehurst et al. ......... 607/3 |
| 7,347,746 | B1 | 3/2008 | He .................... 439/843 |
| 7,623,929 | B1* | 11/2009 | Griffith ................. 607/57 |
| 2001/0031909 | A1 | 10/2001 | Faltys et al. |
| 2003/0036782 | A1 | 2/2003 | Hartley et al. |
| 2003/0097254 | A1 | 5/2003 | Holzrichter et al. |
| 2003/0114905 | A1 | 6/2003 | Kuzma .................. 607/116 |
| 2003/0198953 | A1 | 10/2003 | Spytek et al. |
| 2004/0015204 | A1 | 1/2004 | Whitehurst et al. ........ 607/48 |
| 2004/0015205 | A1 | 1/2004 | Whitehurst et al. ........ 607/48 |
| 2004/0044383 | A1 | 3/2004 | Woods et al. |
| 2004/0082985 | A1 | 4/2004 | Faltys et al. |
| 2004/0136556 | A1 | 7/2004 | Litvak et al. |
| 2005/0137650 | A1 | 6/2005 | Litvak et al. |
| 2005/0137651 | A1 | 6/2005 | Litvak et al. ............ 607/57 |
| 2005/0209652 | A1 | 9/2005 | Whitehurst ............. 607/39 |
| 2005/0240229 | A1 | 10/2005 | Whitehurst ............. 607/39 |
| 2005/0267555 | A1 | 12/2005 | Marnfeldt ............. 606/184 |
| 2006/0100672 | A1 | 5/2006 | Litvak ................. 607/57 |
| 2006/0106446 | A1 | 5/2006 | Fidman et al. ......... 607/137 |
| 2006/0161204 | A1 | 7/2006 | Colvin et al. ............ 607/2 |
| 2006/0167521 | A1 | 7/2006 | He et al. .............. 607/36 |
| 2006/0184204 | A1 | 8/2006 | He .................... 607/61 |
| 2006/0195143 | A1 | 8/2006 | McClure ............. 607/20 |
| 2006/0212087 | A1 | 9/2006 | Haller ................ 607/41 |
| 2006/0229688 | A1 | 10/2006 | McClure et al. ....... 607/72 |
| 2006/0271109 | A1 | 11/2006 | Kuzma ............... 607/2 |
| 2007/0021800 | A1 | 1/2007 | Whitehurst et al. ..... 607/45 |
| 2007/0049988 | A1 | 3/2007 | Carbunaru ........... 607/116 |
| 2007/0055308 | A1 | 3/2007 | Haller et al. .......... 607/2 |
| 2007/0066997 | A1 | 3/2007 | He .................. 607/3 |
| 2007/0100395 | A1 | 5/2007 | Ibrahim ............. 607/60 |
| 2007/0112403 | A1 | 5/2007 | Moffitt .............. 607/116 |
| 2007/0112404 | A1 | 5/2007 | Mann ................ 607/2 |
| 2007/0123938 | A1 | 5/2007 | Haller et al. .......... 607/2 |
| 2007/0219595 | A1 | 9/2007 | He .................. 607/61 |
| 2007/0293785 | A1 | 12/2007 | Litvak ............... 600/559 |
| 2008/0085023 | A1 | 4/2008 | Kulkarni et al. ........ 381/312 |

FOREIGN PATENT DOCUMENTS

| | | |
|---|---|---|
| WO | 02/09808 | 2/2002 |
| WO | 03/015863 | 2/2003 |
| WO | 2004/043537 | 5/2004 |
| WO | 2006/053101 A1 | 5/2006 |
| WO | 2007/030496 A1 | 3/2007 |
| WO | 2007/059343 A2 | 5/2007 |
| WO | 2007/130782 A1 | 11/2007 |

OTHER PUBLICATIONS

U.S. Appl. No. 11/139,296, filed May 26, 2005, R. Carbunaru.
U.S. Appl. No. 11/178,054, filed Jul. 8, 2005, Faltys.
U.S. Appl. No. 11/226,777, filed Sep. 13, 2005, M.A. Faltys.
U.S. Appl. No. 11/261,432, filed Oct. 28, 2005, A.E. Mann.
U.S. Appl. No. 11/262,055, filed Dec. 28, 2005, G.Y. Fridman.
U.S. Appl. No. 11/285,983, filed Nov. 23, 2005.
U.S. Appl. No. 11/386,198, filed Mar. 21, 2006, A. Saoji.
U.S. Appl. No. 11/387,206, filed Mar. 23, 2006, W.V. Harrison.
U.S. Appl. No. 11/534,933, filed Sep. 25, 2006, M. Faltys.
U.S. Appl. No. 11/541,117, filed Sep. 2, 2006.
U.S. Appl. No. 11/565,564, filed Nov. 30, 2006, Fister.
U.S. Appl. No. 11/765,395, filed Jun. 19, 2007, Fridman et al.
U.S. Appl. No. 60/665,171, filed Mar. 24, 2005, W.V. Harrison.
U.S. Appl. No. 60/669,822, filed Apr. 5, 2005, K.H. McClure.
U.S. Appl. No. 60/950,324, filed Jul. 17, 2007, Fridman et al.
U.S. Appl. No. 60/975,111, filed Sep. 25, 2007, Kulkarni et al.
Eddington et al., "Auditory Prostheses Research with Multiple Channel Intracochlear Stimulation in Man," Ann Otol Rhinol. Laryngol 87:1.
Harnsberger et al., "Perceptual 'vowel spaces' of Cochlear Implant Users: Implications for the Study of Auditory Adaptation to Spectral Shift," J Acoust Soc Am, 109(5 Part 1):2135.
Loizon, P.C., "Mimicking the Human Ear," IEEE Signal Processing Magazine, pp. 101.
McDermott, H.J. and C.M. McKay, "Pitch Ranking with Nonsimultaneous Dual-Electrode Electrical Stimulation of the Cochlea," J Acoust Soc Am (96) 1, Jul. 1994, 155-162.
Morse, R.P. and G.F. Meyer, "The Practical Use of Noise to Improve Speech Coding by Analogue Cochlear Implants," Chaos, Solutions and Fractals, 11(12): 1885.
Rubinstein et al., "The Neurophysiological Effects of Simulated Auditory Prosthesis Simulation," Second Quarterly Progress Report NO1.
Scheirer et al., "Construction and Evaluation of Robust Multifeature Speech/Music Discriminator," 1997 IEEE International Conference on Acoustics, Speech, and Signal Processing: Apr. 21.
Smith et al., "Chimaeric Sounds Reveal Dichotomies in Auditory Perception," Nature 416 (6876): 87.
Van Wieringen and J. Wouters, "Comparison of Procedures to Determine Electrical Stimulation Thresholds in Cochlear Implant Users," Ear and Hearing, 22(6): 528.
Zeng et al., "Loudness of Simple and Complex Stimuli in Electric Hearing," Annals of Otology, Rhinology & Laryngology, 104(9):235.
Zhang et al., "Loudness of dynamic Stimuli in Acoustic and Electric Hearing," J Acoust Soc Am, 102(5 Part 1): 2925-2934 (Nov. 1997).

* cited by examiner

ESTIMATING FLAP THICKNESS FOR COCHLEAR IMPLANTS

CROSS REFERENCE TO RELATED APPLICATIONS

This application is a continuation of U.S. patent application Ser. No. 11/016,604, filed Dec. 16, 2004, to which priority is claimed and which is incorporate herein by reference in its entirety.

BACKGROUND

The following description relates to cochlear implants, and more particularly to fully implantable cochlear implant systems that allow profoundly deaf persons to hear sounds without the need for wearing or carrying external hearing devices or components. For such implants, it is useful to estimate the patient's flap thickness around the area of the implant (in general, the thickness of the flap of skin on the patient's skull) using measurements of radiofrequency transfer efficiency.

Cochlear implants provide a new mechanism for hearing when a hearing aid is insufficient to overcome a hearing impairment. Advances in cochlear implants make it possible today for otherwise completely deaf individuals to hear. Unlike a hearing aid that amplifies sound to make it loud enough for an impaired ear to detect it, a cochlear implant bypasses the damaged part of the anatomy and sends sound signals directly to the auditory nerve, thus restoring the ability to hear sound in an individual who is deaf.

Typical cochlear implant systems today have four components: a sound processor; a transmitter; an implant; and an array of electrodes. The sound processor and transmitter usually reside outside the human body, while the implant and electrodes are surgically implanted in an individual's head, near the affected ear.

The sound processor can be a small hand-held unit, stored in a pocket or attached to a belt clip, or hung around an individual's ear. The transmitter is typically a small unit that transmits information received from the sound processor to the implant. The transmitter usually sends a radiofrequency (RF) signal to the implant through the individual's skin. The implant receives the information and converts digital information into electrical signals, which are sent to the electrode array.

In many systems today, the transmitter is positioned behind the ear the transmitter and implant, which attract each other across the skin flap and hold the transmitter in place. Usually, inside of the transmitter there is a coil that is used to inductively or magnetically couple a modulated AC carrier signal to a similar coil that is included within the implant. In order to achieve efficient coupling without suffering significant losses in the signal energy, it is important that the external coil within the transmitter be properly aligned with the internal coil within the implant.

Flap thickness, which is the thickness of the skin and accompanying tissue between the two magnets, can vary by individual. Flap thickness can have an impact on efficient coupling between the transmitter and implant. Furthermore, flap thickness data is helpful in determining the appropriate strength of the securing magnets. Magnets with too much strength can lead to discomfort and necrosis, while magnets with too little strength do not secure the transmitter in place. Current measurement techniques for flap thickness include the use of needles and gauss meters, which can be both painful and inconvenient.

SUMMARY

The present inventors recognized a need for determining flap thickness with sufficient specificity to enable the design of RF systems that are optimized for the average patient while still covering the range of distances between the transmitter and receiver in the implant, and also for determining the optimum magnet strength for any individual.

In one aspect, a method of estimating a thickness of a skin flap of a human subject having an implanted cochlear implant includes collecting measurement data by performing a plurality of measurements of an amount of electrical energy stored in the cochlear implant while varying a stimulation load signal or a power level, or a combination of both, applied to the cochlear implant. The collected measurement data is compared with predetermined calibration data, and the skin flap thickness is estimated based at least in part on a result of the comparison.

In another aspect, a method of obtaining reference data for use in determining flap thickness is described. The method includes transmitting energy at a first power level across a first flap simulator having a first known thickness and obtaining a first set of calibration data representative of a first measurement of tank voltage. The method also includes transmitting energy at the first power level across a second flap simulator having a second known thickness different from the first known thickness and obtaining a second set of calibration data representative of a second measurement of tank voltage. The method may also include transmitting energy at a second power level across the first flap simulator and obtaining a third set of calibration data representative of a third measurement of tank voltage, and transmitting energy at the second power level across the second flap simulator and obtaining a fourth set of calibration data representative of a fourth measurement of tank voltage.

In another aspect, a method of obtaining reference data for use in determining flap includes obtaining two or more measurements of tank voltage across a flap simulator of a first known thickness, wherein a different power level is applied with respect to each measurement. The method may further include obtaining two or more measurements of tank voltage across a flap simulator of a second known thickness, wherein a different power level is applied with respect to each measurement.

In another aspect, a method of obtaining reference data for use in determining flap thickness includes measuring an amount of electrical energy stored in a cochlear implant using a predetermined stimulation load and a predetermined power level. The method also includes altering at least one of a stimulation load value and a power level value, and repeating the electrical energy storage measurement using the at least one altered value.

In another aspect, a flap thickness measurement system includes a reference cochlear stimulation system. The reference cochlear stimulation system includes a sound processor, a transmitter that transmits a telemetric signal, and a cochlear stimulator having a receiver that receives the telemetric signal and transmits a signal back to the transmitter. The system further includes one or more flap simulators having one or more known thicknesses that is positioned between the transmitter and receiver. Also included is a microprocessor that receives and processes data representative of tank voltage from the reference cochlear stimulation system.

The details of one or more embodiments are set forth in the accompanying drawings and the description below. Other features and advantages will be apparent from the description and drawings and from the claims.

DESCRIPTION OF DRAWINGS

Like reference symbols in the various drawings indicate like elements.

DETAILED DESCRIPTION

Figure 1A:
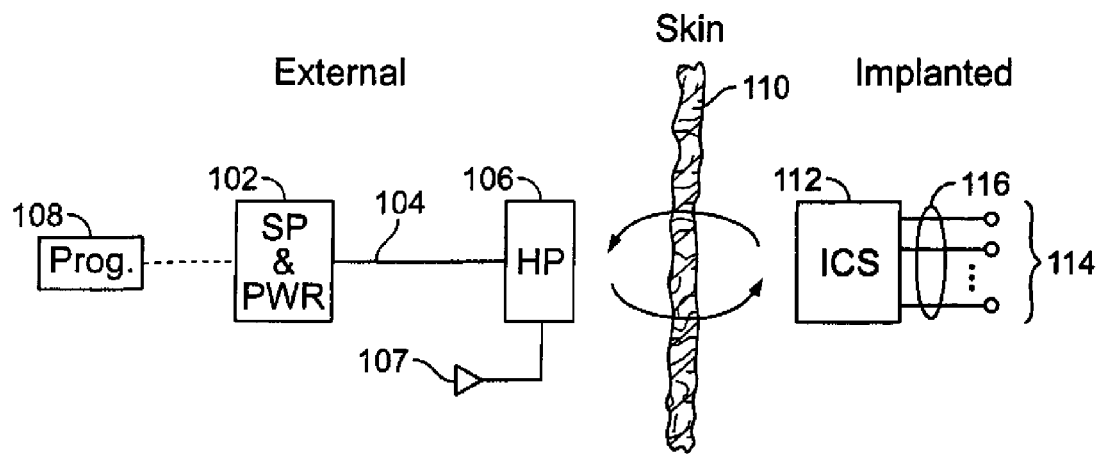
FIG. 1A illustrates a typical cochlear stimulation system as currently used by many patients, including an implantable cochlear stimulator (ICS) that is inductively coupled with an external headpiece (HP) connected with an external speech processor (SP) and power source.

An overview of an exemplary cochlear stimulation system is provided below in connection with FIGS. 1A and 1B. The following description is exemplary and the devices, systems, and methods described herein can be used with other types and other configurations of cochlear stimulation systems.

A representative cochlear stimulation system of the type currently used by many patients is fully described, e.g., in U.S. Pat. No. 5,776,172 ("the '172 patent"), incorporated herein by reference. As described in the '172 patent, and as illustrated in FIG. 1A, such existing system includes implanted and external components. The external components include a speech processor (SP), a power source (e.g., a replaceable battery), and a headpiece (HP) 106. The SP and power source are typically housed within a wearable unit 102 that is worn or carried by the patient. The wearable unit is electrically connected to the HP 106 via a cable 104. A microphone 107 is also included as part of the headpiece 106.

The implanted components include an implantable cochlear stimulator (ICS) 112 and an array of electrodes 114. The electrode array 114 is intended for implantation within the cochlear of the patient. The ICS 112 is implanted behind the ear, so as to reside near the scalp. The electrode array 114 is permanently connected to the ICS by way of a multi-conductor implantable cable 116.

Inside of the headpiece 106 is a coil (transmitter) that is used to inductively or magnetically couple a modulated AC carrier signal to a similar coil (receiver) that is included within the ICS 112. In order to achieve efficient coupling, without suffering significant losses in the signal energy, it is important that the external coil within the headpiece be properly aligned with the internal coil inside the ICS. To achieve proper alignment, a magnet is typically included within both the headpiece 106 and the ICS 112, and the resulting magnetic attraction between the two magnets not only aligns the coils, as desired, but also provides a holding force that maintains the headpiece 106 securely against the scalp or skin flap 110 of the patient.

In use, a carrier signal is generated by circuitry within the wearable unit 102 using energy derived from the power source within the speech processor unit 102. Such carrier signal, which is an AC signal, is conveyed over the cable to the headpiece 106 where it is inductively coupled to the coil within the ICS 112. There it is rectified and filtered and provides a DC power source for operation of the circuitry within the ICS 112. Sounds are sensed through the external microphone 107, amplified and processed by circuitry included within the speech processor unit 102, and converted to appropriate stimulation signals in accordance with a selected speech processing strategy by circuitry within the speech processor unit 102. These stimulation signals modulate the carrier signal that transfers power to the ICS 112. The ICS includes an appropriate demodulation circuit that recovers the stimulation signals from the modulated carrier and applies them to the electrodes within the electrode array 114. The stimulation signals identify which electrodes, or electrode pairs, are to be stimulated, the sequence of stimulation and the intensity of the stimulation.

Some embodiments of the ICS 112, as indicated in the '172 patent, include a back telemetry feature that allows data signals to be transmitted from the ICS 112 to the headpiece 106, and hence to the Speech Processor 102. Such back telemetry data provides important feedback information to the speech processor regarding the operation of the ICS, including the amount of power needed by the ICS. See, e.g., U.S. Pat. No. 5,876,425, issued to the same assignee as the present application, and also incorporated herein by reference.

When adjustment or fitting or other diagnostic routines need to be carried out, an external programming unit 108 is detachably connected to the SP unit 102. Through use of the external programmer 108, a clinician, or other medical personnel, is able to select the best speech processing strategy for the patient, as well as set other variables associated with the stimulation process. See, e.g., U.S. Pat. No. 5,626,629, incorporated herein by reference, for a description of a representative fitting/diagnostic process.

Figure 1B:
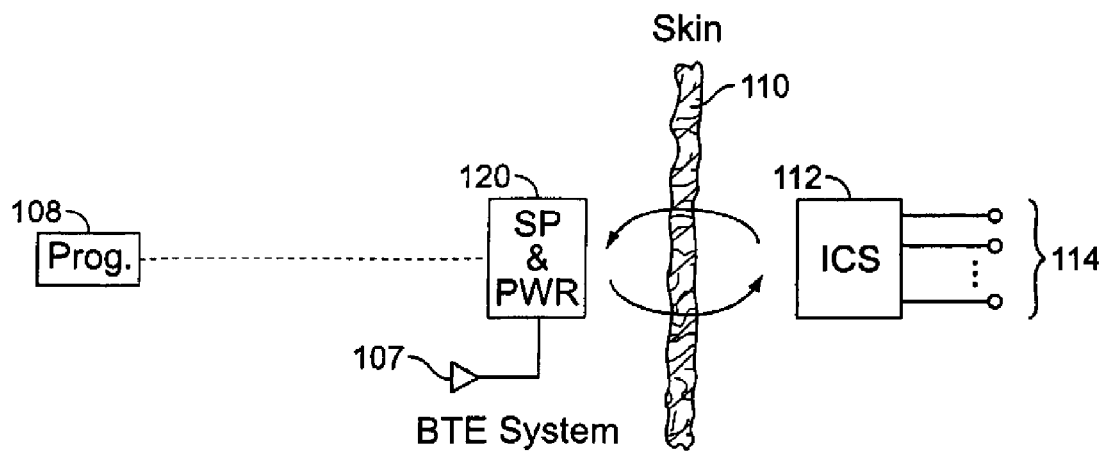
FIG. 1B illustrates a behind-the-ear (BTE) cochlear stimulation system that includes an implanted cochlear stimulator (ICS) and an external BTE unit that includes a power source, a speech processor and a microphone.

FIG. 1B depicts a behind-the-ear (BTE) unit 120. The BTE unit 120 may include everything that was previously included within the wearable unit 102, only in a much smaller volume. The BTE unit 120 thus includes a suitable power source, as well as the circuitry needed for performing a desired speech processing function. With the BTE unit 120, there is thus no need for the cable 104, and the patient simply wears the BTE unit behind his or her ear, where it is hardly noticed, especially if the patient has hair to cover the BTE unit. Advantageously, the batteries employed within the wearable unit 102 (FIG. 1A) or the BTE unit 120 (FIG. 1B) may be readily replaced when needed.

The present inventors recognized a need to determine the skin flap 110 thickness in a noninvasive and convenient manner. Measurements of flap 110 thickness enable the design of RF systems for cochlear stimulation systems that are optimized for the average patient while still covering the range of distances between the transmitter in the HP 106 or SP/PWR 120 and receiver in the ICS 112.

Figure 2:
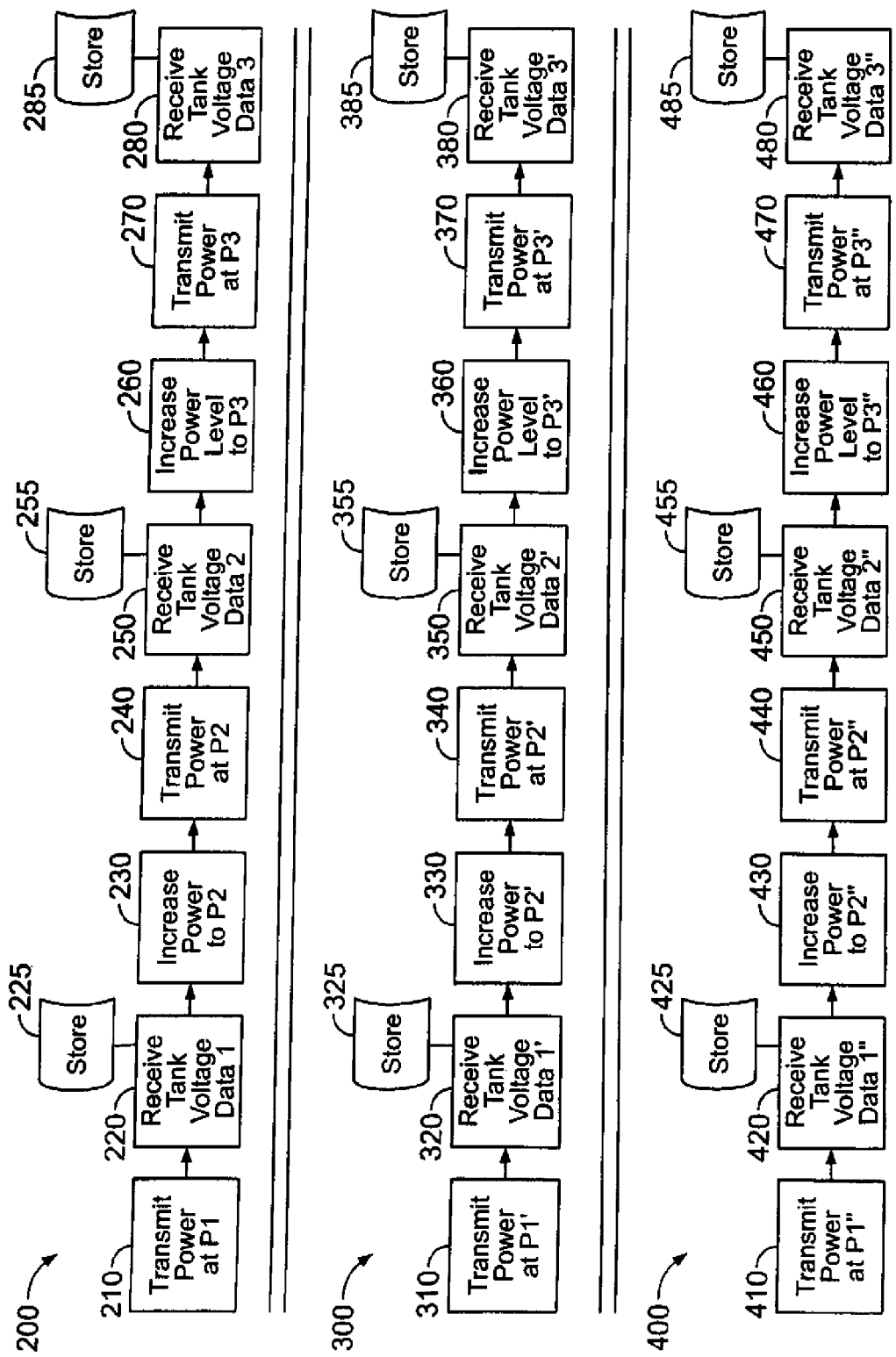
FIG. 2 is a flow chart depicting a method for obtaining reference data for use in determining flap thickness.

To obtain reliable measurements estimating flap thickness, reference or calibration data is first collected prior to obtaining a particular individual's measurements. FIG. 2 is a flowchart that depicts a method for obtaining reference data for use in determining flap thickness. A first series of steps for obtaining data representing tank voltage measurements associated with a first flap simulator having a known thickness is shown at 200. A second series of steps for obtaining data representing tank voltage measurements associated with a flap simulator having a known thickness that is different from the flap simulator used in 200 is shown at 300. A third series of steps for obtaining data representing tank voltage measurements associated with a flap simulator having a known thickness that is different from the flap simulator used in 200 and 300 is shown at 400. The three series of steps 200, 300 and 400 can be performed substantially simultaneously as shown in FIG. 2 or sequentially in any order. Thus, steps 200-280 may be performed prior to steps 300-380, which may be performed prior to steps 400-480. Alternatively, steps 400-480 may be performed first followed by steps 200-280 or 300-380. Alternatively, steps 300-380 may be performed first followed by steps 200-280 or 400-480.

Steps 200-280 will next be discussed. At steps 200-280, a flap simulator of a known thickness is used to simulate a human flap of skin just behind the ear. A reference cochlear stimulation system in accordance with those described herein is used. The flap simulator is placed in between a transmitter and receiver of the reference cochlear stimulation system. In an implanted cochlear stimulation system, the transmitter would be secured to the outside of the individual's head and the receiver would be implanted underneath the skin flap juxtaposed with the transmitter. In steps 200-280, an implanted cochlear stimulation system is simulated by placing the flap simulator in between the transmitter and receiver. Energy is transmitted by the transmitter through the flap simulator to the receiver at a first power level P1 at 210. The energy transmitted can be RF energy or any other type of suitable telemetric energy. Tank voltage data, which is a measure of transfer efficiency, is transmitted back to the transmitter from the receiver and received by a microprocessor at 220. The data is stored by the microprocessor at 225. Power is increased at 230 and a corresponding energy transmitted again by the transmitter through the flap simulator to the receiver at 240 at a second power level P2. Tank voltage data is transmitted back to the transmitter from the receiver and received by the microprocessor at 250. The data is stored by the microprocessor at 255. Power is increased again at 260 and a corresponding energy transmitted again by the transmitter through the flap simulator to the receiver at 270 at a third power level P3. Tank voltage is transmitted back to the transmitter from the receiver and received by the microprocessor at 280. The data is stored by the microprocessor at 285. Steps 260-280 can be repeated an n number of times with an increase in power each time to collect as much reference data as is practicable or necessary.

Steps 310-380 can be carried out simultaneously with steps 210-280, before steps 210-280, or after steps 210-280 as shown in FIG. 2. Steps 310-380 are identical to steps 210-280 except that the flap simulator that is used has a different thickness from the flap simulator used in steps 210-280. The flap simulator can either be thicker than or thinner than the flap simulator used in steps 210-280. Altering the distance between the transmitter and receiver by altering the thickness of the flap simulator is one way to vary the stimulation load that is applied. In the case where steps 210-280 and 310-380 are performed sequentially or at different times, then one flap simulator that has an adjustable thickness can be used for both series of steps, with the thickness adjusted so that it varies between steps 210-280 and 310-380. Steps 360-380 can be repeated an n number of times with an increase in power each time to collect as much reference data as is practicable or necessary.

Another way to alter the stimulation load is to vary the current being applied in addition to varying the distance. Therefore, rather than only altering the thickness of the flap simulator, steps 310-380 can be performed under conditions in which the current being applied is varied as well. Thus, steps 310-380 would be identical to steps 210-280 except that an increased or a decreased level of current is applied in addition to using a flap simulator having a thickness that is different from the one used in steps 210-280.

Steps 410-480 can be carried out simultaneously with steps 210-280 and/or steps 310-380, before steps 210-280 and/or 310-380, or after steps 210-280 and/or 310-380. In other words, the three respective series of steps, 210-280, 310-380, and 410-480 can be carried at any time with respect to one another as shown in FIG. 2. Steps 410-480 are identical to steps 210-280 and 310-380 except that the flap simulator that is used has a different thickness from the flap simulators used in steps 210-280 and 310-380. Altering the distance between the transmitter and receiver by altering the thickness of the flap simulator is one way to vary the stimulation load that is applied. In the case where the three series of steps are performed sequentially or at different times, then one flap simulator that has an adjustable thickness can be used for all three series of steps, with the thickness adjusted so that it varies between steps 210-280, 310-380 and 410-480. Steps 460-480 can be repeated an n number of times with an increase in power each time to collect as much reference data as is practicable or necessary.

Again, another way to alter the stimulation load is to vary the current being applied in addition to altering the thickness of the flap simulator. Therefore, rather than altering the thickness of the flap simulator, steps 410-480 can be performed under conditions in which the current being applied is varied as well. Thus, steps 410-480 would be identical to steps 210-280 and 310-380 except that an increased or a decreased level of current is applied in addition to using a flap simulator having a thickness that is different from the ones used in steps 210-280 and 310-380.

As shown at steps 225, 255, 285, 325, 355, 385, 425, 455, and 485, tank voltage data is obtained and stored. This data is later used as reference or calibration data to estimate flap thickness for patient's that use implanted cochlear stimulation systems.

The method described in FIG. 2 is one exemplary embodiment of a method of obtaining reference or calibration data, in which reference data at three different power levels and three different stimulation loads (i.e., flap simulator thicknesses and/or current levels) are used. Other embodiments may use as few as two power levels and two stimulation loads (i.e., different flap simulator thicknesses or current levels) or as many as five, six, seven, eight, nine, ten or n number of power levels and stimulation loads, with n representing any number above ten.

Figure 3:
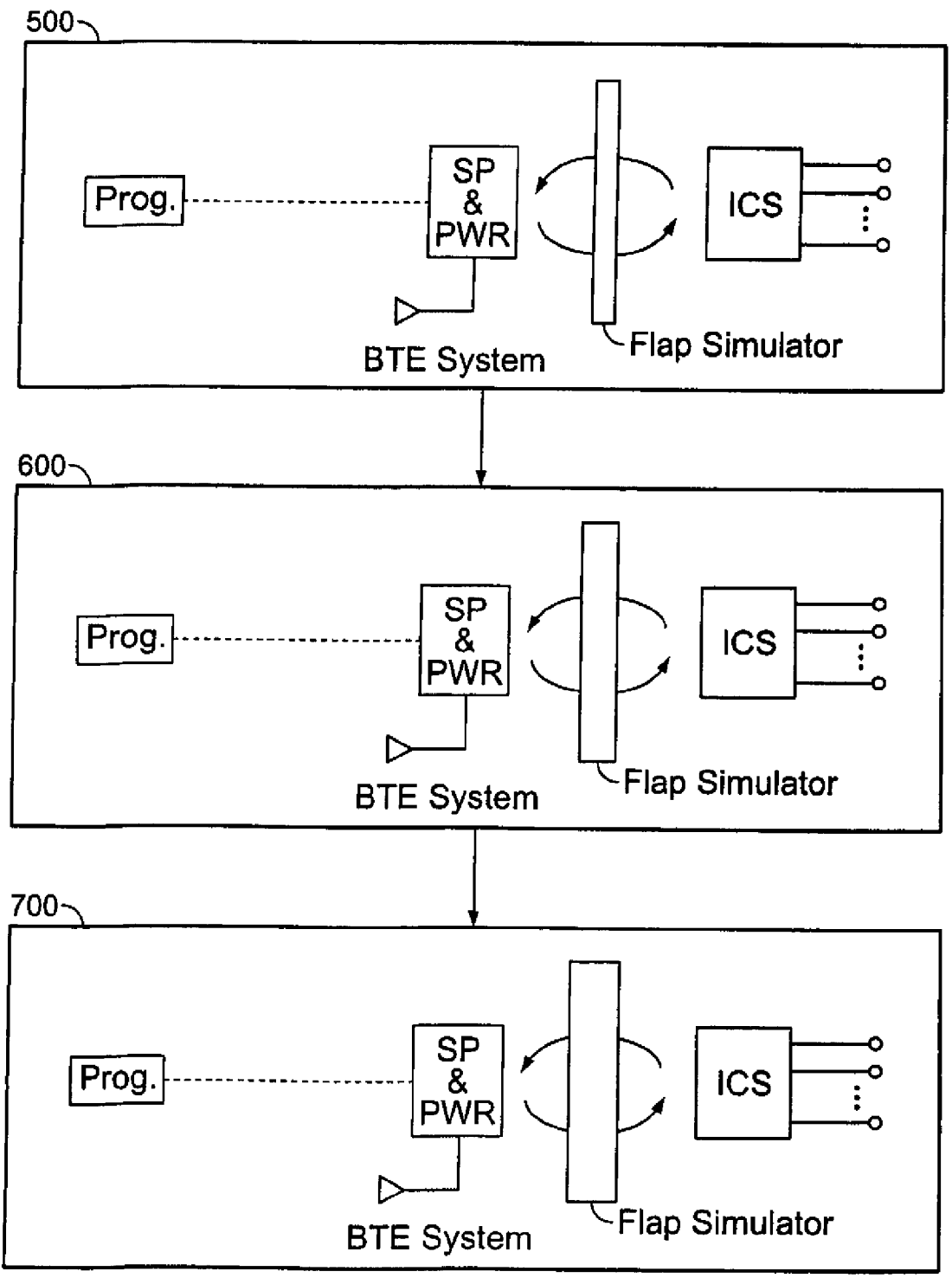
FIG. 3 is a flow chart depicting a method for obtaining reference data for use in determining flap thickness in accordance with another embodiment.

FIG. 3 represents another method of obtaining reference or calibration data. At step 500, a flap simulator of a known thickness is used to simulate a human flap of skin just behind the ear. As shown in FIG. 3, a reference cochlear stimulation system in accordance with those described herein is used. The flap simulator is placed in between a transmitter (SP & PWR) and receiver (ICS) of the reference cochlear stimulation system. In an implanted cochlear stimulation system, the transmitter would be secured to the outside of the individual's head and the receiver would be implanted underneath the skin flap juxtaposed with the transmitter. In steps 500, 600, and 700, an implanted cochlear stimulation system is simulated by placing the flap simulator in between the transmitter and receiver. Energy is transmitted by the transmitter through the flap simulator to the receiver at a known and predetermined power level. Tank voltage data, which is a measure of transfer efficiency, is transmitted back to the transmitter from the receiver and received by a microprocessor integrated with the speech processor and power source (PROG). The data is stored by the microprocessor for later use. The microprocessor may alternatively be a standalone computer that communicates directly with the headpiece speech processor and power source in any manner known to those of skill in the art, such as through a wireless, serial, or parallel connection.

In addition, current can be varied across a predetermined range while recording tank voltage data. This can be accomplished in a continuous process or a sequential process. In either case, tank voltage data is transmitted, either continuously or sequentially, to the transmitter from the receiver and received by the microprocessor. By varying current while measuring tank voltage data, additional data points are gathered for later correlation with data received from human subjects who are fitted for cochlear implants and/or cochlear implant magnets.

A difference between steps 500, 600, and 700 is that the flap simulator has a different thickness in each step. The flap thickness of the flap simulator is depicted as increasing from step 500 to 700, with the flap simulator having the greatest thickness at step 700. Steps 500-700 can be performed sequentially as shown in FIG. 3, simultaneously, or at different times in random order. If they are performed simultaneously, then three separate flap simulators having three different thicknesses can be used. If they are performed sequentially or at different times, then one flap simulator that has an adjustable thickness can be used for all three steps, with the thickness adjusted so that it varies between steps 500, 600, and 700.

Also, any of steps 500-700 can be repeated an n number of times using a different power level (i.e., RF strength) each time in a predetermined range of power levels so that tank voltage data for different powers levels and different loads can be collected and used as reference or calibration data. This can be accomplished in a continuous process or a sequential process in which both power level and current are being varied while collecting tank voltage data.

Figure 4:
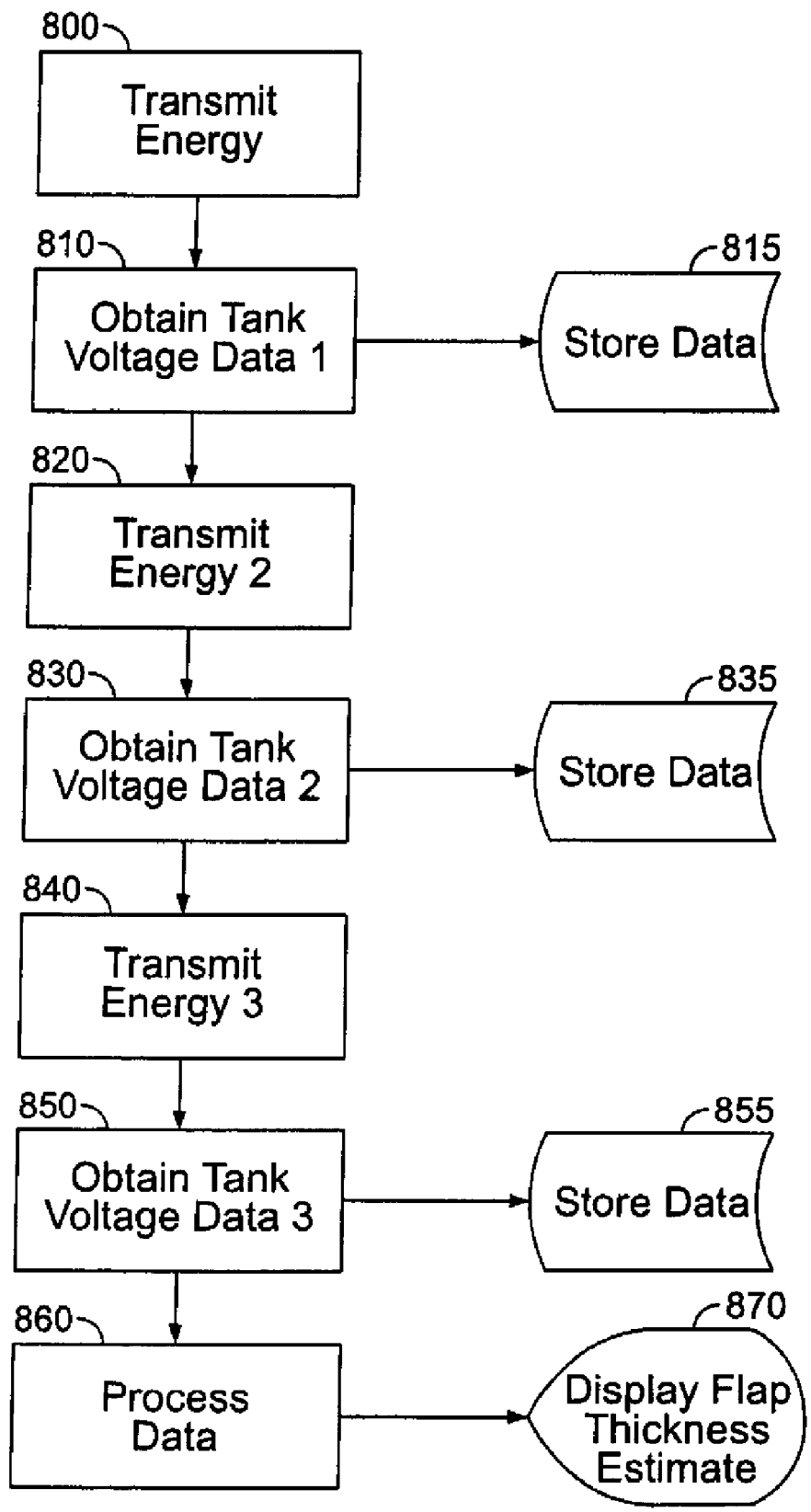
FIG. 4 is a flow chart depicting a method for estimating flap thickness for a cochlear stimulation system.

FIG. 4 is a flowchart showing steps associated with a method of estimating flap thickness. The first step, not shown, is to implant a cochlear stimulation system, such as anyone of those described herein or incorporated herein by reference. As shown in FIGS. 1A and 1B, an implantable cochlear stimulator 112 is implanted underneath a flap of skin behind an individual's ear. A headpiece 106 or speech processor and power source 120 is secured against the individual's head juxtaposed with the ICS 112 on the outer side of the flap of skin.

After the cochlear stimulation system is in place, at step 800 energy is transmitted at a first known power level by the transmitter associated with the headpiece or speech processor and power source across the individual's flap of skin and to the receiver associated with the ICS on the other side of the skin flap. Stimulating current transmitted at step 800 may also be a known value. Tank voltage data is transmitted back to the transmitter from the receiver and received by a microprocessor in communication with the cochlear stimulation system at 810. The tank voltage data is stored by the microprocessor at 815. The microprocessor can be a standalone computer that communicates directly with the headpiece 106 or speech processor and power source 120 in any manner known to those of skill in the art, such as through a wireless, serial, or parallel connection. Alternatively, the microprocessor can be integrated with the headpiece 106 or speech processor and power source 120. In either case, the microprocessor either has a display integrated with it, or communicates with a display. At step 820 energy is transmitted at a second known power level different from the first power level by the transmitter across the individual's skin flap and to the receiver on the other side of the skin flap. Stimulation current may also be a known value that is either the same or different from the stimulation current applied at step 800. Tank voltage data is transmitted back to the transmitter from the receiver and received by the microprocessor at 830. Tank voltage data is stored by the microprocessor at 835. At step 840 energy is transmitted at a third known power level different from the first and second power levels by the transmitter across the individual's skin flap and to the receiver on the other side of the skin flap. Stimulation current may also be a known value that is either the same as or different from the stimulation current applied at steps 800 and 820. Tank voltage data is transmitted back to the transmitter from the receiver and received by the microprocessor at 850. Tank voltage data is stored by the microprocessor at 855. The data is correlated with the reference or calibration data obtained by the processes described above and processed at 860. An estimate of the thickness of the individual's flap of skin is displayed on a display at 870.

The three power levels transmitted at steps 800, 820, and 840 can correspond with the power levels transmitted during the acquisition of calibration or reference data, but this is not a strict requirement. Also, steps 800-815, 820-835 and 840-855, may be replicated an n number of times to obtain an n number of sets of tank voltage data with the power level changing each time.

In one alternative embodiment, steps 840-855 may be eliminated, consequently obtaining only two sets of tank voltage data to correlate with reference data. In another alternative embodiment, steps 820-855 may be eliminated, consequently obtaining only one set of tank voltage data to correlate with reference data.

Figure 5:
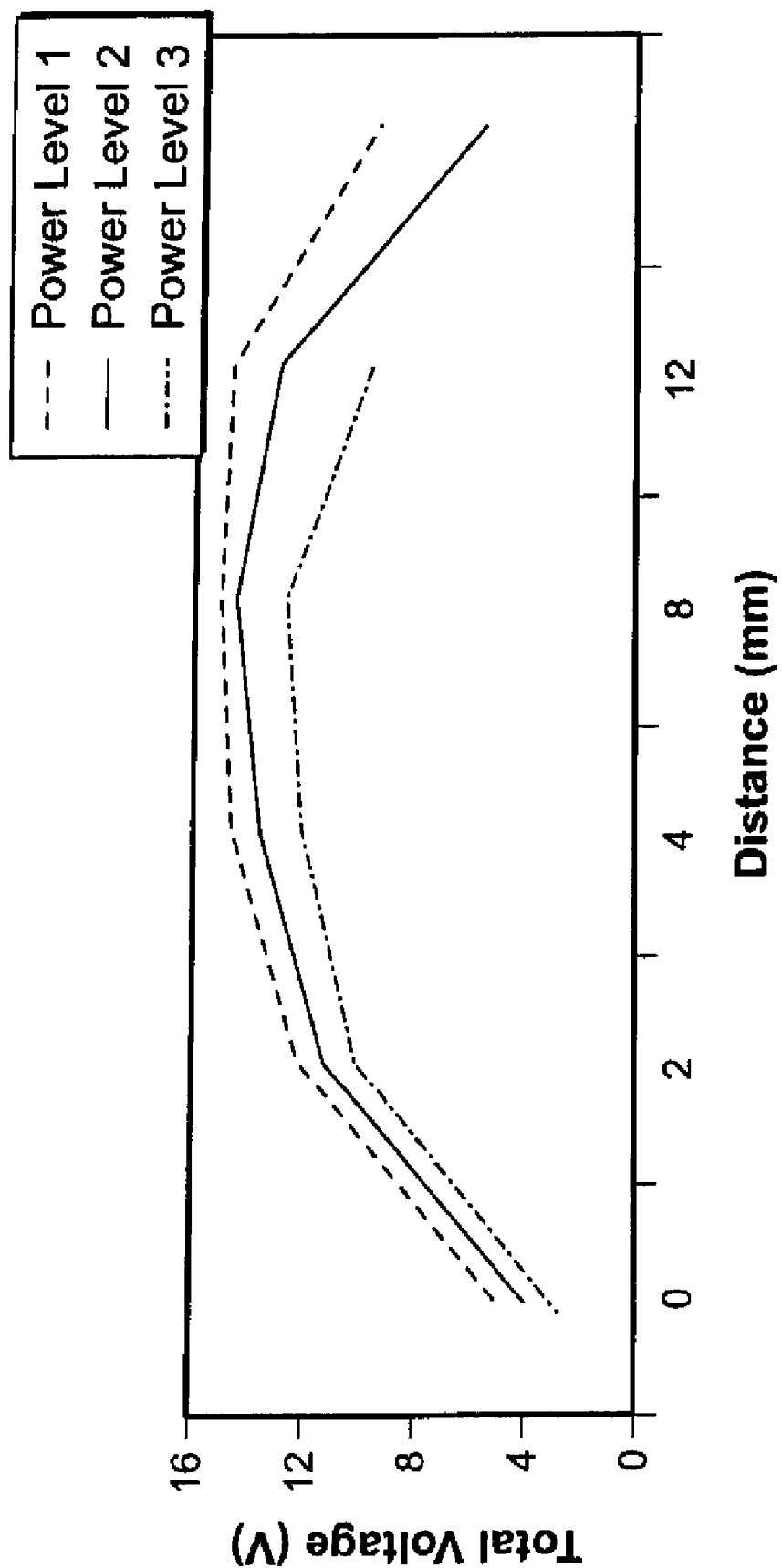
FIG. 5 is a graph depicting a measurement of an individual's flap thickness plotted against three reference measurements taken at three power levels.

In FIG. 5 the solid lines represent calibration or reference data at three power levels and one stimulation load. The individual's tank voltage is plotted with the horizontal lines and the point of intersection of these lines with the corresponding calibration line is the estimate flap thickness. Tank voltages that are either too low or too high (due to saturation) can be discarded in the estimation. Statistical methods (such as a median) may be used to calculate a value. Ambiguities in the correct result, since there can be two points of intersection with the calibration data, can be resolved by observing an increase or decrease in tank voltage with increasing load. Load can be either distance or stimulation. Increasing tank voltage would indicate that the lower estimate is correct.

Figure 6:
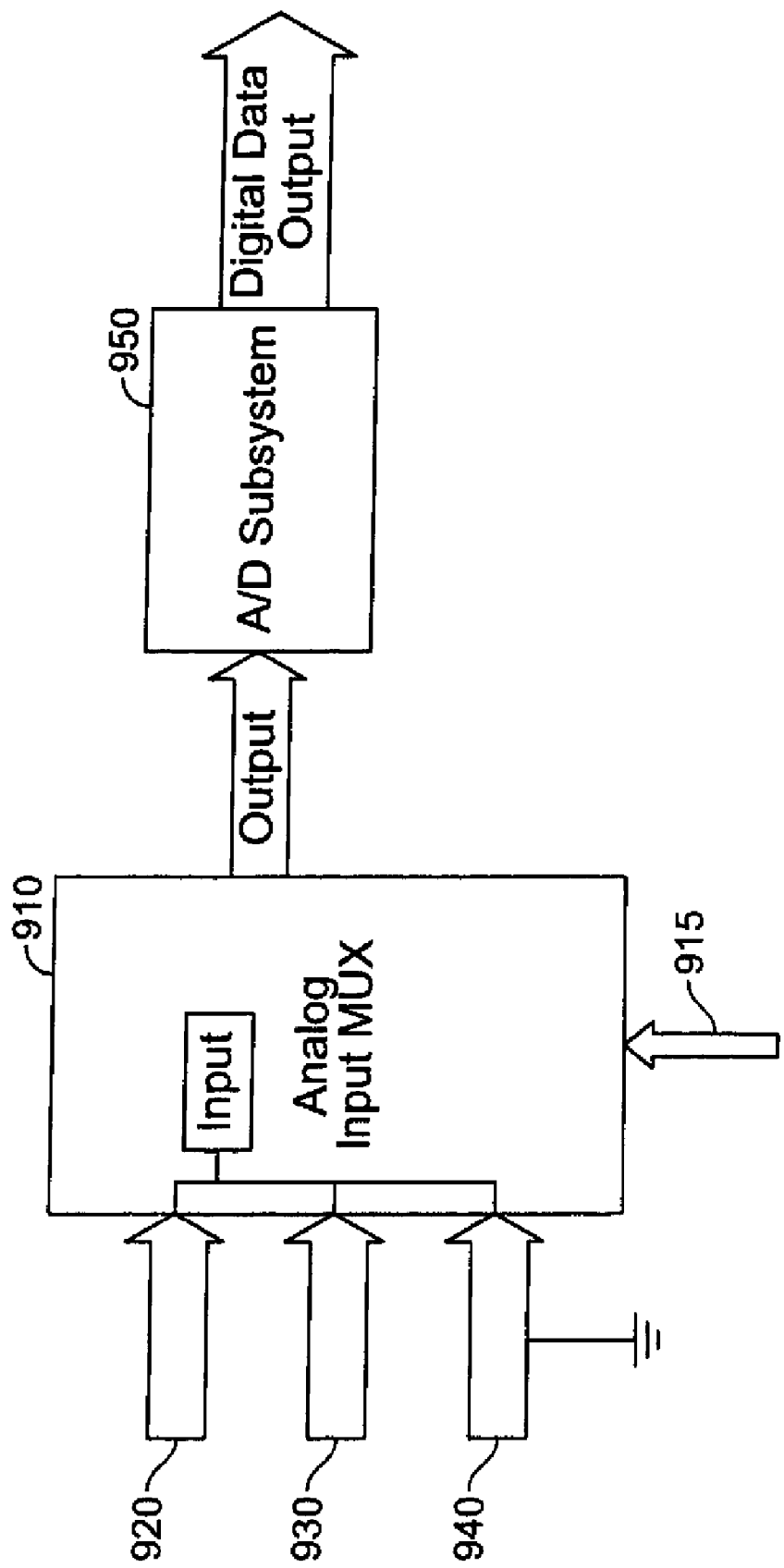
FIG. 6 is a diagram of one embodiment of an analog-to-digital conversion system associated with an implantable cochlear stimulator.

FIG. 6 is a diagram of an implementation of an analog-to-digital conversion (ADC) system associated with an implantable cochlear stimulator, such as the ICS 112 shown in FIGS. 1A and 1B. The INPUT multiplexor 910 ("the MUX") when performing the flap thickness estimation technique described here, is used to shunt current away from the stimulation electrodes 920. In one implementation, the MUX 910 is an analog multiplexor, but it could be digital instead in other implementations. The MUX 910 has the ability, through application of appropriate control signals 915, to connect together all of its input signals and its output signals simultaneously. All of the electrodes, including the stimulation electrodes 920, the stapedius electrodes 930 and the indifferent (ground) electrodes 940, which are connected to signal ground, are substantially simultaneously connected to the outputs of MUX 910, which is connected to an A/D subsystem 950. In one implementation, there are a total of twenty input electrodes: sixteen stimulation electrodes 920, two stapedius electrodes 930, and two indifferent electrodes 940. The impedance to current flow through the MUX 910 to ground 940 is much smaller than the impedance through the stimulation electrodes 920 and tissue and back through the ground electrodes 940. Therefore, almost all of the current is shunted internally to ground so that virtually no current is applied to the stimulation electrodes and thus the patient does not hear the stimulation. This enables the production of fixed loads on a cochlear implant and the measurement of the transfer function at levels that an individual would not otherwise be able to tolerate. In one implementation, the whole ADC system depicted in FIG. 6 can be implemented on a single application specific integrated circuit (ASIC).

Other embodiments are within the scope of the following claims.

What is claimed:

1. A method of configuring a cochlear implant system, the method comprising:
   collecting individualistic data in a medical implant system comprising a medical implant implanted within a user and an external portion affixed external to the user, wherein the individualistic data comprises a plurality of measurements indicative of energy received at the medical implant in response to transmission from the external portion at a plurality of different powers;
   comparing the collected individualistic data with reference data, wherein reference data is indicative of distances between a transmitter and a receiver in a reference medical implant system; and
   configuring the cochlear implant system based at least in part on a result of the comparison.

2. The method of claim 1, wherein configuring the cochlear implant system comprises controlling transmission to the cochlear implant.

3. The method of claim 1, wherein comparing the collected individualistic data with the collected reference data comprises estimating a distance between the medical implant and the external portion.

4. The method of claim 1, wherein the measurements indicative of energy received at the medical implant comprise tank voltages.

5. The method of claim 1, wherein the medical implant comprises a cochlear implant, and wherein the external portion comprises a speech processor.

6. The method of claim 1, wherein configuring the cochlear implant system comprises configuring the power of signal transmission between the external portion and the medical implant.

7. The method of claim 1, wherein comparing the collected individualistic data with reference data occurs at a microcontroller associated with the external headpiece.

8. A method of configuring a cochlear implant system comprising a cochlear implant implanted within a user and an external headpiece affixed external to the user, the method comprising:
   transmitting a plurality of signals from a transmitter in the external headpiece affixed external to the user to a receiver in the cochlear implant implanted within the user, wherein each signal comprises a different power;
   measuring a voltage at the receiver in response to each signal; and
   determining a distance between the transmitter and the receiver by comparing the measured voltages to reference data.

9. The method of claim 8, wherein the transmitter and the receiver both comprise a coil.

10. The method of claim 8, wherein the measured voltages are transmitted from the cochlear implant to the external headpiece.

11. The method of claim 10, wherein the measured voltages are processed by a microprocessor associated with the external headpiece.

12. The method of claim 8, wherein the measured voltages comprise voltages of a tank circuit in the cochlear implant.

13. The method of claim 8, wherein the reference data comprises data defining receiver-to-transmitter distance as a function of transmitter power and receiver voltage as taken from a reference system.

14. The method of claim 13, wherein the reference system is external to the user.

15. The method of claim 13, further comprising as initial steps in the method, collecting the reference data, comprising:
   obtaining a plurality of first receiver voltages at a receiver in the reference system in response to a plurality of first signals transmitted from a transmitter in the reference system, wherein each first signal comprises a different power, wherein the first signals are transmitted across a first flap simulator of a first thickness; and
   obtaining a plurality of second receiver voltages at the receiver in the reference system in response to a plurality of second signals transmitted from the transmitter in the reference system, wherein each second signal comprises a different power, wherein the second signals are transmitted across a second flap simulator of a first thickness different from the first thickness.

16. The method of claim 8, further comprising configuring signal transmission between the transmitter and the receiver based on the determined distance.

17. The method of claim 8, wherein the cochlear implant comprises a first magnet and the external headpiece comprises a second magnet attracted by a strength to the first magnet to hold the external headpiece in place relative to the cochlear implant, and further comprising determining the strength of the first and second magnets based on the determined distance.

18. A cochlear implant system, comprising:
   an external headpiece, comprising
      a transmitter, and
      a microprocessor for storing reference data, wherein the reference data comprises data indicative of a receiver-to-transmitter distance as taken from a reference system, wherein the microprocessor further is configured to compare individualistic data received from the cochlear implant to the reference data to estimate a distance between the transmitter and the receiver; and
   a cochlear implant comprising the receiver, the cochlear implant configured to transmit the individualistic data to the external headpiece, wherein the individualistic data comprises a plurality of measurements indicative of energy received at the cochlear implant in response to transmission from the transmitter at a plurality of different powers.

19. The system of claim 18, wherein the measurements indicative of energy received at the cochlear implant comprise tank voltages.

20. The system of claim 18, wherein the microprocessor is further configured to configure a power of signal transmission between the external portion and the medical implant based on the estimated distance.

21. The system of claim 18, wherein the transmitter and the receiver both comprise a coil.

22. The system of claim 18, wherein the reference system is external to the user.

23. The system of claim 18, wherein the reference data was procured in accordance with a method, the method comprising:

obtaining a plurality of first receiver voltages at a receiver in the reference system in response to a plurality of first signals transmitted from a transmitter in the reference system, wherein each first signal comprises a different power, wherein the first signals are transmitted across a first flap simulator of a first thickness; and obtaining a plurality of second receiver voltages at the receiver in the reference system in response to a plurality of second signals transmitted from the transmitter in the reference system, wherein each second signal comprises a different power, wherein the second signals are transmitted across a second flap simulator of a first thickness different from the first thickness.

* * * * *

UNITED STATES PATENT AND TRADEMARK OFFICE
CERTIFICATE OF CORRECTION

| | | |
|---|---|---|
| PATENT NO. | : 7,920,924 B2 | Page 1 of 1 |
| APPLICATION NO. | : 12/244082 | |
| DATED | : April 5, 2011 | |
| INVENTOR(S) | : Lakshmi Narayan Mishra | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 328 days.

Signed and Sealed this
Seventh Day of June, 2011

David J. Kappos
*Director of the United States Patent and Trademark Office*